(12) United States Patent
Johnson et al.

(10) Patent No.: US 11,864,972 B2
(45) Date of Patent: Jan. 9, 2024

(54) LIGHT-BASED ALIGNER SEATING APPARATUS AND METHODS

(71) Applicant: PerioTech, LLC, Palm Beach Gardens, FL (US)

(72) Inventors: Richard Johnson, Palm Beach Gardens, FL (US); Nicholas Puro, Sunny Isles Beach, FL (US)

(73) Assignee: PerioTech, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/679,726

(22) Filed: Feb. 24, 2022

(65) Prior Publication Data
US 2023/0263597 A1 Aug. 24, 2023

(51) Int. Cl.
*A61C 7/08* (2006.01)
*A61C 19/06* (2006.01)
*A61N 5/06* (2006.01)

(52) U.S. Cl.
CPC ............... *A61C 7/08* (2013.01); *A61C 19/06* (2013.01); *A61N 5/0603* (2013.01); *A61N 2005/0606* (2013.01)

(58) Field of Classification Search
CPC ........ A61C 7/08; A61C 19/06; A61N 5/0603; A61N 2005/0606
See application file for complete search history.

(56) References Cited

U.S. PATENT DOCUMENTS

| 5,487,662 | A | 1/1996 | Kipke et al. |
| 6,976,841 | B1 | 12/2005 | Osterwalder |
| 9,655,691 | B2 | 5/2017 | Li et al. |
| 9,730,780 | B2 | 8/2017 | Brawn et al. |
| 9,974,630 | B2 * | 5/2018 | Heacock .............. A61C 1/0046 |
| 10,111,729 | B1 * | 10/2018 | Lowe ..................... A61C 7/008 |
| 10,220,221 | B2 * | 3/2019 | Wu ....................... A61N 5/0603 |
| 10,758,330 | B2 * | 9/2020 | Vermeulen ........... A61C 19/066 |
| 10,918,882 | B2 * | 2/2021 | Demarest ............ A61C 19/066 |

(Continued)

FOREIGN PATENT DOCUMENTS

| WO | WO-0032131 A1 * | 6/2000 | .............. A61C 7/00 |
| WO | WO 2013/155632 A1 | 10/2013 | |

(Continued)

OTHER PUBLICATIONS

[No Author], "SmartTrack Aligner Material", Material Safety Data Sheet, Align Technology, Inc., 2560 Orchard Parkway, San Jose, CA, (Dec. 8, 2015), 6 pages.

(Continued)

*Primary Examiner* — Heidi M Eide
*Assistant Examiner* — Lina Faraj
(74) *Attorney, Agent, or Firm* — Finnegan, Henderson, Farabow, Garrett & Dunner LLP

(57) ABSTRACT

A device and method for seating orthodontic aligners over the dentition of a user includes a light-based device having a bite plate or mouthpiece, with light-emitting elements, for contacting the aligners. Instructions are provided for using of the light-based aligner seating device by placing the mouthpiece over the aligners, applying light radiation during a predetermined number of sessions throughout a predetermined treatment period, wherein the seating and the fit between the aligners and teeth are better than without use of the light-based device.

16 Claims, 4 Drawing Sheets

(56) References Cited

U.S. PATENT DOCUMENTS

| | | | |
|---|---|---|---|
| 11,110,291 B2* | 9/2021 | Bloch | A61C 19/066 |
| 11,141,603 B2* | 10/2021 | Bloch | A61N 5/062 |
| 11,382,727 B1* | 7/2022 | Marghalani | A61C 9/0006 |
| 11,458,003 B2* | 10/2022 | Vermeulen | A61C 19/066 |
| 2002/0051951 A1* | 5/2002 | Chishti | A61C 7/08 433/6 |
| 2002/0142258 A1* | 10/2002 | Chishti | A61C 7/08 433/8 |
| 2005/0233276 A1* | 10/2005 | Kopelman | A61C 7/08 433/3 |
| 2008/0032253 A1 | 2/2008 | Montgomery et al. | |
| 2008/0233541 A1 | 9/2008 | De Vreese et al. | |
| 2015/0140502 A1* | 5/2015 | Brawn | A61C 19/06 433/29 |
| 2015/0164618 A1 | 6/2015 | Heacock et al. | |
| 2017/0080249 A1* | 3/2017 | Brawn | A61N 5/0603 |
| 2018/0078338 A1* | 3/2018 | Way | A61C 7/00 |
| 2019/0029522 A1* | 1/2019 | Sato | G06T 7/75 |
| 2019/0046297 A1* | 2/2019 | Kopelman | A61C 19/003 |
| 2019/0083202 A1* | 3/2019 | Brawn | A61C 8/0006 |
| 2019/0099241 A1 | 4/2019 | Way et al. | |
| 2019/0102880 A1* | 4/2019 | Parpara | G06T 17/10 |
| 2020/0107908 A1* | 4/2020 | Aronson | A61C 7/16 |
| 2020/0261185 A1* | 8/2020 | Hunter | A61C 9/0053 |
| 2020/0261186 A1* | 8/2020 | Hunter | A61C 7/08 |
| 2020/0315745 A1* | 10/2020 | Way | A61C 19/02 |
| 2021/0145546 A1* | 5/2021 | Lemchen | A61C 19/04 |
| 2022/0118274 A1* | 4/2022 | Brawn | A61N 5/0616 |
| 2022/0273401 A1* | 9/2022 | Penn | A61C 7/08 |

FOREIGN PATENT DOCUMENTS

| | | | | |
|---|---|---|---|---|
| WO | WO-2015058284 A1 * | 4/2015 | | A61C 19/006 |
| WO | WO 2016/154679 A1 | 10/2016 | | |
| WO | WO-2017147604 A1 * | 8/2017 | | A61C 17/20 |
| WO | WO-2020112735 A2 * | 6/2020 | | A61C 7/00 |

OTHER PUBLICATIONS

Shimizu, N. et al., "Prospect of Relieving Pain Due to Tooth Movement During Orthodontic Treatment Utilizing a Ga—Al•As Diode Laser", SPIE vol. 1984, pp. 275-280.

International Search Report and Written Opinion from International Application No. PCT/US2023/062791 filed Feb. 17, 2023 (9 pages).

* cited by examiner

LIGHT-BASED ALIGNER SEATING APPARATUS AND METHODS

TECHNICAL FIELDS

This disclosure concerns the efficiency of orthodontic treatment, more specifically, devices and methods to facilitate sealant and seating of the aligners using low-level laser light (LLLL) or light-emitting diodes (LED).

BACKGROUND

Orthodontic treatment is typically used to improve the appearance and alignment of crooked, protruding, or crowded teeth and to correct malocclusions. To achieve these goals, orthodontic appliances such as braces, aligners, and retainers can be applied to the patient's teeth. Currently, many people prefer clear aligner treatment because it is aesthetically superior to conventional bracket-and-wire orthodontic braces. Aligners are clear, thin trays that fit tightly over your teeth. They are less noticeable and are widely utilized as a minimally invasive procedure for repositioning misaligned teeth and correcting various orthodontic malocclusions.

Most aligners on the market are made of a thermoplastic material, such as thermoplastic polyurethane (TPU) films formed from a single or multiple layers. To achieve the orthodontic treatment goal, the orthodontic thermoplastic materials are known to have characteristics including biocompatibility, transparency, low hardness, good elasticity, resilience, and resistance.

A sequence of aligners is designed and dimensioned to gradually move the teeth towards the desired position after assessing the current position of the teeth and how they are predicted to change over time. Each set of aligners is worn for 2-3 weeks and moves teeth a small amount at a time. It is usually the case when starting a new aligner in a set of aligners that it may not easily fit to the user's dentition, resulting in a poor fit over the teeth. This is because each aligner in the sequence of aligners is shaped to introduce a geometrical mismatch with respect to the current tooth positions to induce an orthodontic force. Non-adherent orthodontic patients may also find the aligners are difficult to seat after periods of not wearing them. Wearing aligners that are not fitted fully and snugly over the teeth can slow or degrade the treatment and cause unnecessary pain due to misalignment during fitting or wearing. To solve this problem, one prior art solution is the use of so-called aligner chewies to help seat the aligners. These are small compliant cylinders that are about the size of a cotton roll. After the new aligners are put on, biting down on the chewie for 5-10 minutes may help the aligners fit more closely to the teeth. However, the repeated biting or chewing motion may lead to soreness around the jaw, and potential distortion and damage to the aligner. There is also a risk that a patient may swallow a chewie and/or get choked by it. Therefore, it is desired to have a device that is easy to use and secure, and a way to help the aligners fit well to the teeth without adding discomfort to the teeth and jaw muscles or damaging the aligners.

SUMMARY

According to an exemplary embodiment of the present disclosure, a method for seating the aligners is described. The method includes identifying a patient using aligners, providing the patient with a light-based aligner seating device having a mouthpiece, or bite plate, for contacting and directing the light to the seated aligners, and providing instructions for using the light-based aligner seating device. The instruction includes placing the mouthpiece over the aligners and applying light radiation for a predetermined or sufficient time period to allow full seating of the aligners to the teeth. The instructions can also include gently biting down to help properly seat the aligners over the dentition.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

BRIEF DESCRIPTION OF THE DRAWINGS

The accompanying drawings constitute a part of this specification. The drawings illustrate several embodiments of the present disclosure and, together with the description, serve to explain the principles of the disclosed embodiments as set forth in the accompanying claims.

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and together with the description, serve to explain the principles of the disclosure. In the drawings.

Figure 1:
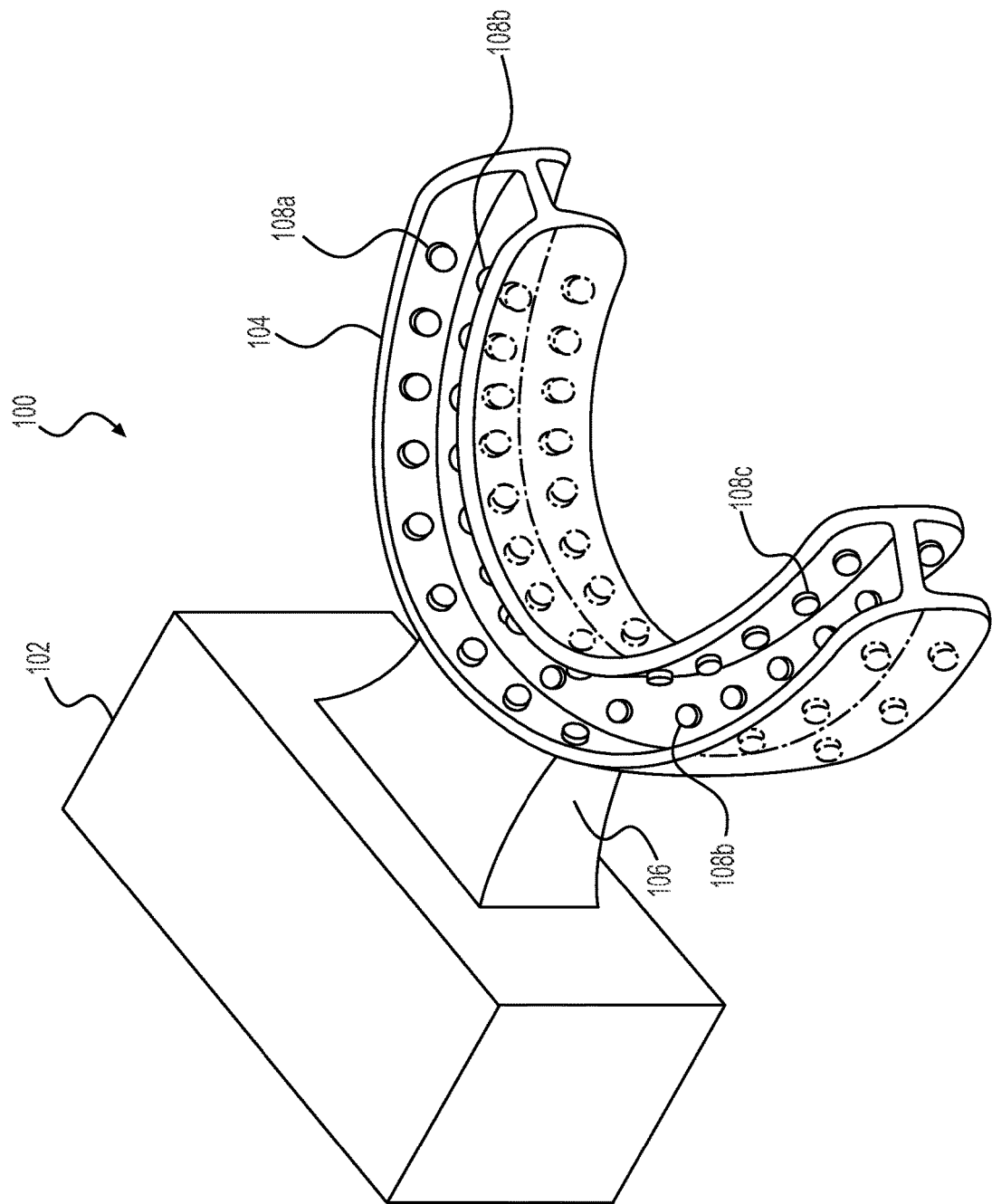
FIG. 1 depicts a top view of an illustrative light-based device according to one aspect of the disclosure.
Figure 2:
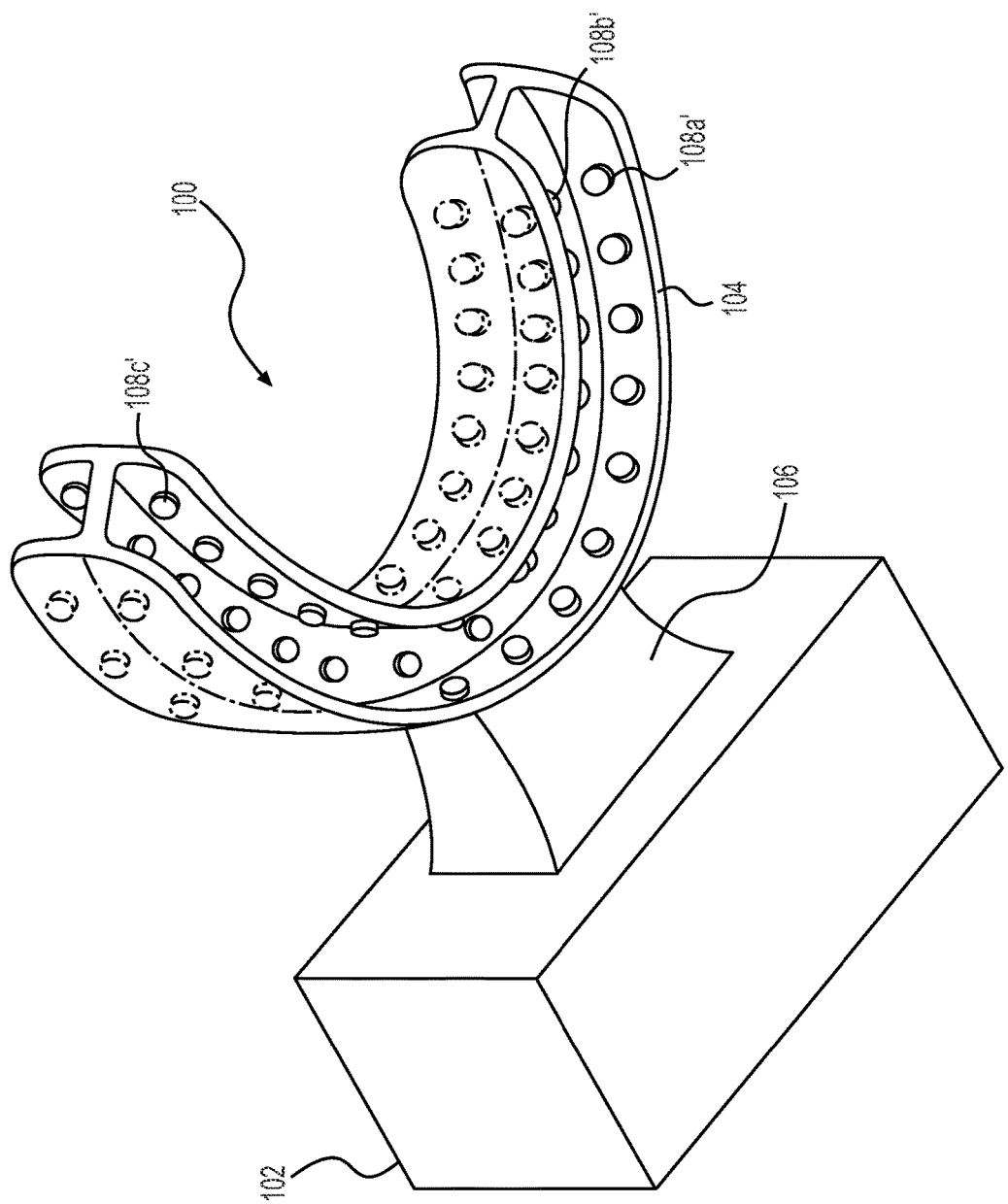
FIG. 2 depicts a bottom view of an illustrative light-based device according to one aspect of the disclosure.

Reference will now be made in detail to exemplary embodiments. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

DETAILED DESCRIPTION

It is to be understood that both the foregoing general description and the following detailed description are exemplary and explanatory only and are not restrictive of the claims.

The disclosed embodiments relate to devices, systems, and methods for seating orthodontic aligners. Advantageously, embodiments of the present disclosure can be implemented to soften the aligners with temporary reversible shape changes. According to some aspects of the present disclosure, use of a light-based aligner seating device with a light source including low-level laser light (LLLL) or light-emitting diodes (LEDs) can soften the aligners temporarily, lead to a better seating and a more positive fit between the aligners and teeth than without. Further advantageously, embodiments of the present disclosure can be implemented to alleviate the discomfort caused by seating aligners and to accelerate the orthodontic process.

The present disclosure refers to aligners, but is also applicable to clear plastic retainers. Frequently, non-adherent patients that have undergone orthodontic treatment find that clear plastic retainers are difficult to seat after periods of retainer disuse. This is because of the natural shifting of the teeth, particularly following orthodontia. The present disclosure can help seat retainers in the same way as seating an aligner used during the course of orthodontia.

In an aspect, with reference to FIGS. 1-4, use of the aligner seating device providing LLLL or LED light radiation for a sufficient period of time after putting on the aligners can improve the seating of the aligners. Without being bound by theory, it is speculated that the photon energy from LLLL or LED directed at the aligners can raise the temperature of the aligners by a predetermined amount that increases elastic flexibility but won't permit permanent deformation. The limited temperature rises for the aligners relaxes the resilient positioning force on the patient's teeth and temporarily softens the aligners. Biting down on the light-based device's mouthpiece or biteplate while the aligners are softer helps to reduce the resistance to the aligner fitting to the dentition. The softened aligners, which provide less resistance while seating, alleviate the difficulty and discomfort of the seating process. When the light-based device is removed from the mouth after the session, the temperature around the aligners drops back to normal oral temperature and the aligners revert to their original shape and hardness. With the aligners properly seated, the aligner over the teeth applies the desired orthodontic forces in specific locations to move the teeth into the designed configuration. The improved fit between the aligner and teeth helps to ensure that the orthodontic forces of the aligner are delivered according to the treatment plan, and help ensure optimal outcomes of the orthodontic treatment process, helping avoid delays and corrections. It should be noted that the concepts described herein can be incorporated into an orthodontic vibration or light-based therapy device or teeth-whitening device as an optional mode, and a separate standalone seating device is not a requirement of the disclosure. It should be further noted that the energy type described herein is not limited to the light source. Other energy types that can soften and temporarily change the stiffness of aligners to better seat over the dentition can be included in, or otherwise incorporated into, the exemplary embodiments described herein.

Described herein are LLLL or LED light-based devices, which in certain embodiments include a mouthpiece configured to transmit light to all or a portion of the patient's aligners on the teeth. In some embodiments, the appliance can be configured to engage with a patient's aligners alone or can be configured to engage with a patient's aligners and gums. The mouthpiece may gently engage with the gum line at or below the gingival margin to provide stimulation to the soft tissue. Such gentle stimulation, as is known in the art, can help to increase blood flow and other cells of repair to the site, in addition to providing light to the aligners covering the teeth. The appliance can be accordingly configured to stimulate one or more aligners, the soft tissue only, or both one or more aligners and the soft tissue.

Referring to FIGS. 1-4, an exemplary dental device 100 includes a mouthpiece 104 operatively connected to a housing 102 via connector 106. The mouthpiece 104 can be separable from the housing 102 for interchangeability between users or for ease of cleaning. The mouthpiece 104 can be configured with one or more aligner-contacting portions, such as a U-shaped biteplate for contacting aligners, gums, or other oral tissues. The mouthpiece 104 can include a plurality of light emitting elements to provide light radiation to each surface of the dentition while wearing the upper and lower aligners.

Figure 3:
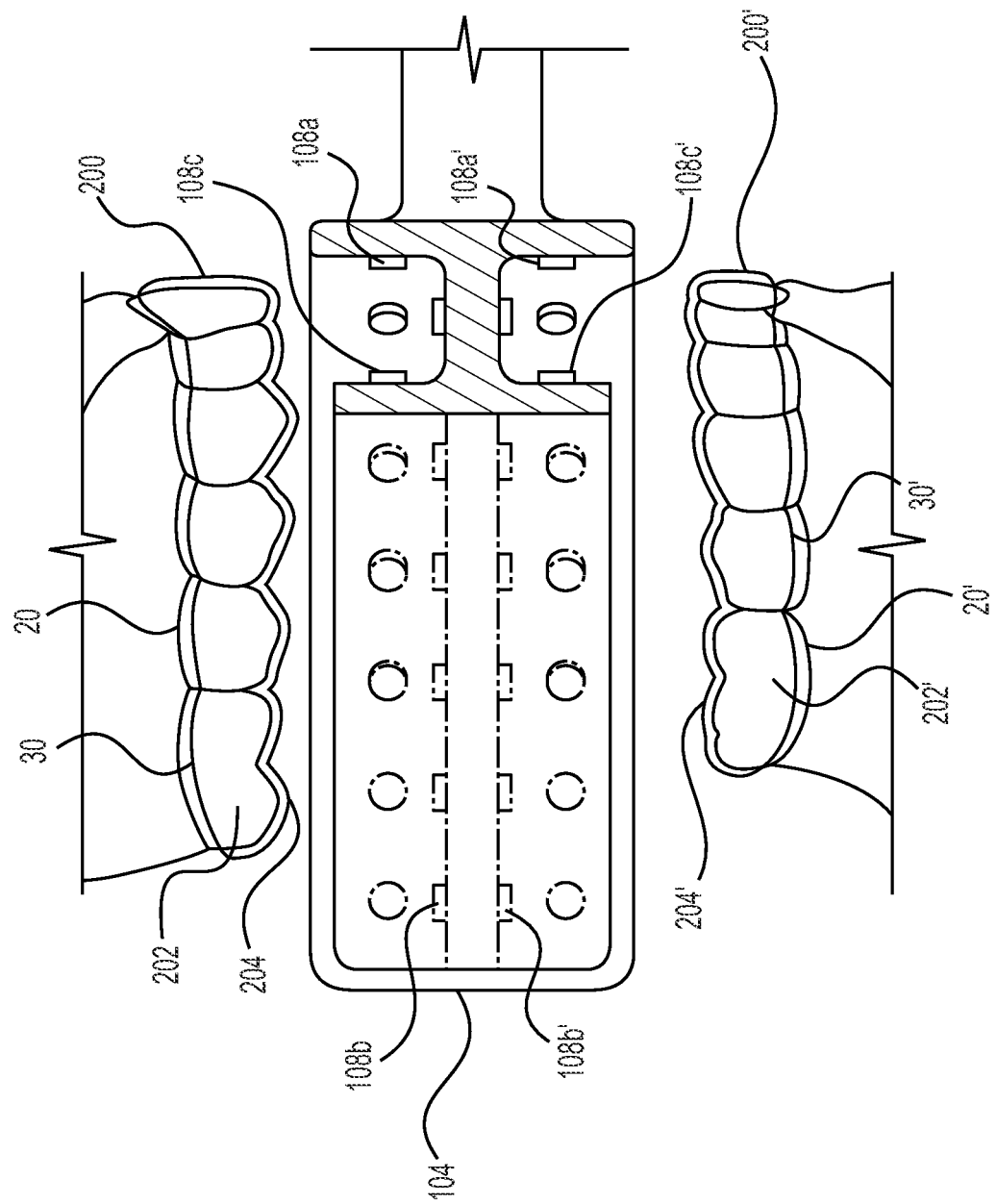
FIG. 3 depicts an illustrative light-based device, such as that depicted in FIGS. 1-2 placed in the mouth of a user, according to one aspect of the disclosure.

As shown in FIG. 3, the upper aligner 30 is seating on the upper dentition 20, and the lower aligner 30' is seating on the lower dentition 20'. The mouthpiece 104 can be placed in between the upper and lower dentition 20, 20'. The mouthpiece includes a plurality of light emitters 108a, 108a' on the outer vertical surfaces to provide light to the labial and buccal surfaces 200, 200'. The mouthpiece 104 includes a plurality of emitting elements 108b, 108b' on the biteplate to provide light to the occlusal and incisal surfaces 204, 204'. The mouthpiece 104 further includes a plurality of emitting elements 108c, 108c' on the inner vertical surface to provide light to the palatal and lingual surfaces 202, 202'.

As shown in FIG. 3, the mouthpiece can include a biteplate which can be appropriately shaped to cover the side surfaces and occlusal surfaces of some or all of a patient's upper and lower aligners. Other shapes for the mouthpiece are possible. A light source can be located in the mouthpiece 104 or the housing 102 to send light to the mouthpiece 104. The housing 102 can also include the electronics to control the light emitting, collect usage and device operation data, collect data from sensors in the mouthpiece or base, and store data in memory. The housing 102 can further include various operational components such as a power supply, data storage, microcontroller, timer, on-off switch, data connector, wireless communications, etc. The housing 102 can include a data interface, which can be wired or wireless, to allow a data connection to other devices. The housing 102 can also include a power interface to allow charging of any onboard power sources, such as batteries or capacitor banks. FIG. 3 depicts an illustrative light-based device 100, such as that described above with reference to FIGS. 1-2, inserted in the mouth of a human user and engaging each surface of the dentition. The mouthpiece of the light-based device 100 can, as described above, be sized and shaped to contact aligners and dental tissue, including part or all of the aligners, specific regions of the gums, or both.

In some embodiments, the parameters, such as wavelength, power, and energy intensity of each light emitting element 108a, 108a', 108b, 108b', 108c, 108c', can be set up and controlled individually by the electronics of the housing 102. Based on the designed orthodontic changes and geometric configuration of the aligners, the force and fit can be varied along the different areas of the dentition. Specifically, the force from the aligner can be higher and the fit between the aligner and teeth can be tighter around the incisor area, while the force from the aligner is close to zero around the molar. Each light emitting element can be controlled and adjusted individually so that it emits light to impart a sufficient amount of pliability to different areas of the aligner. Such varying energy delivery based on the intrinsic construction of the aligner can be derived by utilizing data from the patient's aligner treatment plan used to form the aligners.

Figure 4:
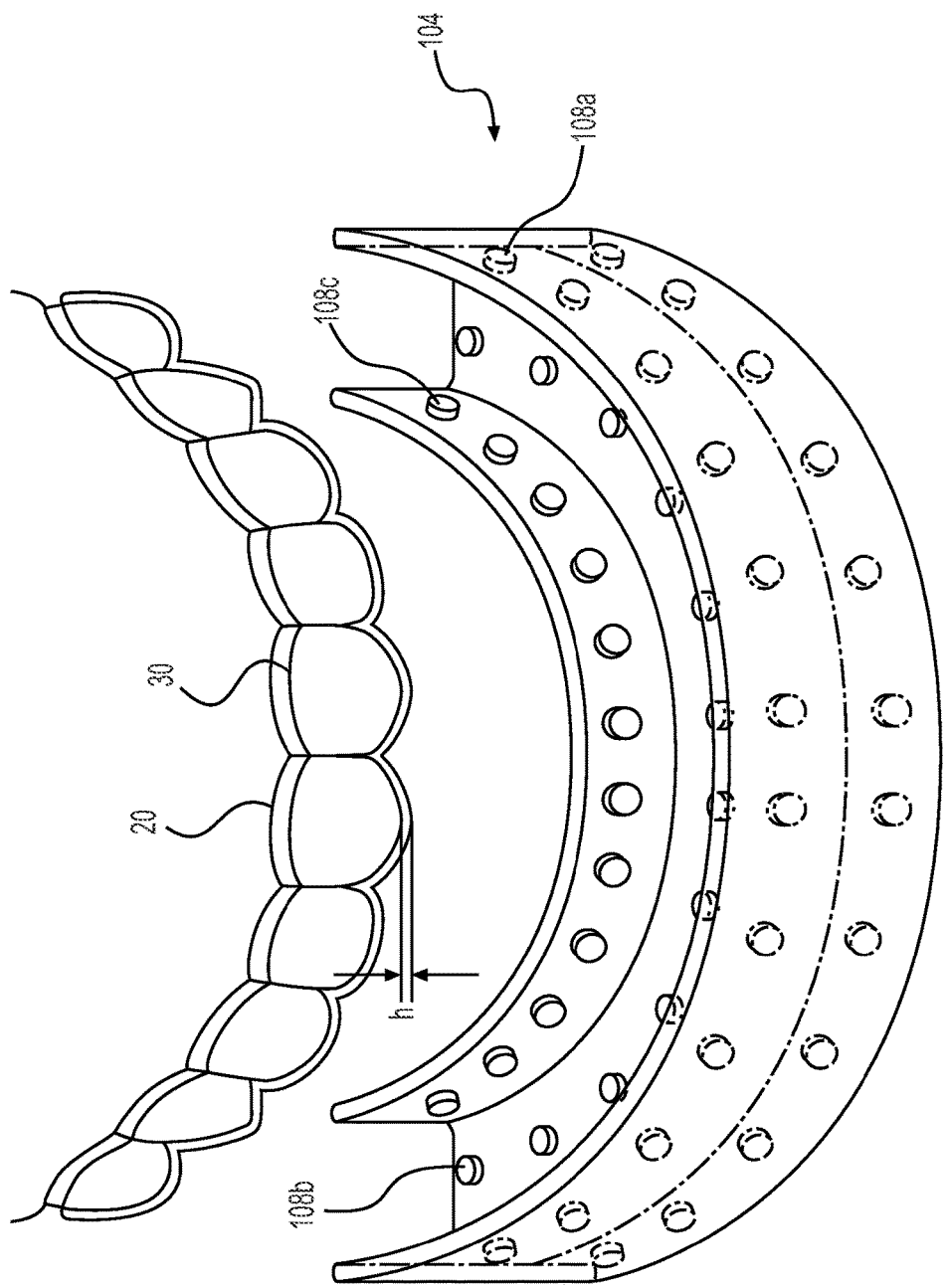
FIG. 4 depicts a front view of an exemplary mouthpiece of an illustrative light-based device, such as that depicted in FIGS. 1-2 used to seat an aligner on the upper-arch dentition of a user.

As shown in FIG. 4, a gap h between the upper dentition's incisal/occlusal surfaces and the bottom of the upper aligner can exist when the upper aligner 30 does not seat on the upper dentition 20 properly. The gap h can be narrowed by using the mouthpiece 104 of the light-based device to soften and fit the aligner on the dentition 20 as the user gently applies bite pressure. In some embodiments, a sensor, or a plurality of sensors on the mouthpiece 104 can be configured to monitor the gap h of each tooth to determine if the aligners are properly seated. A plurality of the photosensors, for example, can be arranged on the array of the mouthpiece. With the tooth geometry data from the orthodontic treatment plan, the expected reflectance of light originating from the light emitters can be calculated by the device. The gap h correlates to the discrepancy between the expected reflectance and the measured reflectance from the light emitters. Comparing the measured data with the pre-set threshold numbers for each tooth, the device can determine if the aligners seat properly on the dentition. The types of the sensors and the ways to monitor the fit are not limited to those listed. Based on the detected fit of the aligners, the device can adjust the parameters of each light emitting element to impart a sufficient amount of pliability to different areas of the aligner. The device can also provide a notification to the user, for example a sound or light indicator, vibration, etc. when full seating has been detected.

In some embodiments, the mouthpiece 104 can include temperature sensors to measure the temperature of each light emitting element, adjust the light based on the measurement results. The mouthpiece 104 can further be configured with temperature sensors to measure the temperature of the upper and lower aligners and dentition, compare the results with a pre-set threshold value, and may turn off the light based on the comparison results.

In some embodiments, the mouthpiece 104 can include humidity sensors to measure the humidity of the aligners and the oral environment and adjust the light parameters based on the detected results.

In some embodiments, the patient can be instructed to use the appliance for a prescribed time and duration to seat the aligners well. In an example, the patient can be instructed to use the appliance for five minutes every time putting on the aligners.

Light can be applied along multiple surfaces of the dentition or selected to be primarily on a single surface, depending on the configuration and composition of the aligner. As shown in FIG. 3, an exemplary embodiment includes a mouthpiece, or biteplate, providing radiation to each surface of the dentition, namely the labial/buccal surfaces 200, 200', palatal/lingual surfaces 202, 202' and occlusal/incisal surfaces 204, 204'. In some embodiments, the device can be instructed or programmed to activate the some or all of the light-emitting elements at a given time or in a sequence to aid in seating the aligner.

Light-Based Aligner Seating Devices

According to an aspect of the present disclosure, a light-based aligner seating device that provide light emitters at one or more predetermined wavelength is provided. In some embodiments the light wavelength is fixed within a lower bound and an upper bound. The lower bound can be greater than about 990 nm, 980 nm, 970 nm, 960 nm, 950 nm, 940 nm, 930 nm, 920 nm, 910 nm, 900 nm, 890 nm, 880 nm, 870 nm, 860 nm, 850 nm, 840 nm, 830 nm, 820 nm, 810 nm, 800 nm, 790 nm, 780 nm, or less. The upper bound can be greater than about 900 nm, 910 nm, 920 nm, 930 nm, 940 nm, 950 nm, 960 nm, 970 nm, 980 nm, 990 nm, 1000 nm, or more. In some embodiments, according to the configuration and consistency of the aligners, the wavelength for each light emitting element varies within a lower and an upper bound. Specifically, when the orthodontic force is high and the aligners are tighter around the incisor area, the wavelengths of the corresponding light emitting elements are on the upper bond; when the orthodontic force is low around the molar area and the aligners will be fitted with molars, the wavelengths of the light are on the lower bond. In some embodiments two or more wavelength, fixed or varying, are employed.

In some embodiments the duration of a seating session can be a predetermined time such as greater than about 30 seconds, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, or more; or specified to be less than about 20 min, 19 min, 18 min, 17 min, 16 min, 15 min, 14 min, 13 min, 12 min, 10 min, 9 min, 8 min, 7 min, 6 min, 5 min, 4 min, 3 min, 2 min, 1 min, 30 seconds, or less.

FIGS. 1-4 depict a light-based aligner seating device, according to an example. The light-based device can include a mouthpiece and a light source connected to each other via a connector. The mouthpiece is configured to be provided between the occlusal surfaces of a user's aligners, and to be bite down by the user to contact the user's aligners during the treatment. The mouthpiece can cover at least one side of the aligners or the area around which a better fit between teeth and aligners is desired. The light source is configured to provide light to light emitters through fiber optics or light guides at one or more preset wavelengths, intensities, and dosages, or can be configured as light-emitting elements such as LEDs mounted on the mouthpiece.

To achieve the maximum desired results of aligners seating on teeth, further studies are still needed to optimize the parameters of light-based device. Such parameters may include wavelength, energy intensity, power intensity, and dosage. Dosage may include duration per use, number of uses per day, or number of days of use, either consecutively or at a certain schedule.

In some embodiments, light may be administered by the light-based device to achieve the predetermined amount of temperature rise to soften the aligners without causing permanent deformation. The thermal effects of the light-based device can be achieved through the control of a selection of parameters, including wavelength, energy intensity, and power intensity of the light radiation of each light emitting element. In some embodiments, the light device may be configured to provide light at a wavelength of 780 nm to 1000 nm. In some embodiments, the light emitting elements of a light-based device can have a power intensity ranging from 20 mw/cm2 to 200 mw/cm2. In some embodiments, the energy intensity of the light from the light-based device can range from 2 to 10 J. With different combinations of the wavelength, energy intensity, and power intensity, the amount of temperature rise can vary from 5 degrees to 20 degrees. The light-based device, when in use, may be configured to provide light at a wavelength as disclosed herein. The phototherapy device, when in use, may be further configured to provide light at an intensity range. In some embodiments, the mouthpiece of a light-based device can have an intensity within a lower bound and an upper bound. The lower bound can be greater than about 20 mW/cm2, 25 mW/cm2, 30 mW/cm2, 35 mW/cm2, 40 mW/cm2, 45 mW/cm2, 50 mW/cm2, 55 mW/cm2, 60 mW/cm2, or more; or less than about 60 mW/cm2, 55 mW/cm2, 50 mW/cm2, 45 mW/cm2, 40 mW/cm2, 35 mW/cm2, 30 mW/cm2, 25 mW/cm2, 20 mW/cm2, or less.

The upper bound can be greater than about 155 mW/cm2, 160 mW/cm2, 165 mW/cm2, 170 mW/cm2, 175 mW/cm2, 180 mW/cm2, 185 mW/cm2, 190 mW/cm2, 195 mW/cm2, 200 mW/cm2, or more; or less than about 200 mW/cm2, 195 mW/cm2, 190 mW/cm2, 185 mW/cm2, 180 mW/cm2, 175 mW/cm2, 170 mW/cm2, 165 mW/cm2, 160 mW/cm2, 155 mW/cm2, or less.

In some embodiments, sensors (not shown) may be added to the light-based aligner seating device, either on the light source device or on the mouthpiece. The sensors may be configured to detect and monitor the parameters of the light, for example, wavelengths, intensities, and dosage. The sensors may also be configured to detect if the user has positioned the mouthpiece correctly. The sensors may further be configured to detect the temperature of the aligners and dentition and turn off the light when the temperature rises to a threshold value. The sensors may further be configured to detect the humidity of the oral environment and turn off the light when the humidity falls to a threshold value. The sensors may further be configured to monitor the fit between the aligners and teeth and adjust the parameters of each light emitting element individually based on the results. The sensors may be photoresistors, infrared sensors, reflectance sensors, proximity sensors, pressure sensors, humidity sensors, temperature sensors, or any combination of them.

In some embodiments, the mouthpiece could be in contact with at least the outer surfaces of aligners and the occlusal surfaces of aligners. The mouthpiece may be configured to be placed in contact with a user's aligners and clamped down by both the occlusal surfaces of the aligners. The mouthpiece can include ridges or be without ridges. The mouthpiece can cover the entire aligners, or only a part of the aligners. The shape of the mouthpiece can be customized to cover only selected surfaces of aligners.

Method For Seating the Aligners

According to yet another aspect of the present disclosure, a method for seating the aligners is described. The method includes providing the mouthpiece of the light-based aligner seating device to a user and providing instructions to the user. The instruction may include placement guidelines and dosage information. The dosage information may include the duration of each seating session, the number of sessions in a day, the number of days, etc. For example, the instruction may instruct a user to use the light-based aligner seating device every time they put the aligners back on the teeth. For example, the instruction may instruct a user to use the light-based aligner seating device every other time aligners are placed on the teeth, after eating and replacing aligners, at bedtime when placing nighttime aligners or retainers, etc.

In some embodiments, the method may further include configuring the light source to provide light emitting to the mouthpiece. The LLLL or LED light may eventually be applied to the aligners sitting on teeth with gaps through the mouthpiece. The light emitting parameters (e.g., wavelengths, intensities, etc.) for each emitting elements can be adjusted by selecting preset values or fine-tuned by users, technicians, or healthcare professionals.

According to yet another aspect of the present disclosure, a method for accelerating seating aligners using a light-based seating device is described. The method includes identifying a patient using aligners for orthodontic treatment, applying light radiation to the aligners while the user gently bites down, and removing the light-based seating device when the aligners are seated, wherein the seating is faster and/or causes less discomfort to the user than without.

The foregoing descriptions have been presented for purposes of illustration. They are not exhaustive and are not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

It should be noted that, the relational terms herein such as "first" and "second" are used only to differentiate an entity or operation from another entity or operation, and do not require or imply any actual relationship or sequence between these entities or operations. Moreover, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the terms "and/or" and "or" encompass all possible combinations, except where infeasible. For example, if it is stated that a device may include A or B, then, unless specifically stated otherwise or infeasible, the device may include A, or B, or A and B. As a second example, if it is stated that a device may include A, B, or C, then, unless specifically stated otherwise or infeasible, the device may include A, or B, or C, or A and B, or A and C, or B and C, or A and B and C.

It is appreciated that the above-described embodiments can be implemented by hardware, or software (program codes), or a combination of hardware and software. If implemented by software, it may be stored in the above-described computer-readable media. The software, when executed by the processor can perform the disclosed methods. The computing units and other functional units described in this disclosure can be implemented by hardware, or software, or a combination of hardware and software. One of ordinary skill in the art will also understand that multiple ones of the above-described modules/units may be combined as one module/unit, and each of the above-described modules/units may be further divided into a plurality of sub-modules/sub-units.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the disclosure disclosed herein. It is intended that the specification and examples be considered as exemplary only, with a true scope and spirit of the disclosure being indicated by the following claims. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A method for seating one or more orthodontic aligner, comprising:
   identifying a patient using one or more orthodontic aligner;
   providing the patient with a light-based aligner seating device having a mouthpiece comprising:
   a light source, wherein the light source comprises a plurality of emitters for contacting and directing the light to the one or more orthodontic aligner; and
   a plurality of sensors to determine a gap between an expected reflectance and a measured reflectance from the light source to determine if the aligners seat properly on the dentition;
   wherein the aligner seating device can adjust a plurality of parameters of each emitter to impart a sufficient amount of pliability to different areas of the aligner based on the detected fit of the aligners
   providing instructions for using the light-based aligner seating device, the instructions comprising: placing the mouthpiece over the one or more orthodontic aligner;
   applying light radiation for a session to allow full seating of the one or more orthodontic aligner on the teeth.

2. The method of claim 1, wherein the emitters are light emitting diodes (LEDs).

3. The method of claim 1, wherein the light source includes a laser.

4. The method of claim 3, wherein the laser includes a low-level laser light.

5. The method of claim 1, wherein a wavelength of the light source is ranging from 780 nm to 1000 nm.

6. The method of claim 1, wherein a power intensity of the light source is ranging from 20 mW/cm$^2$ to 200 mW/cm$^2$.

7. The method of claim 1, wherein an energy intensity of the light source is ranging from 2 J to 10 J.

8. The method of claim 1, wherein the session time is from 30 seconds to 5 minutes.

9. The method of claim 1, where the session is repeated every time right after the one or more orthodontic aligner are put on the teeth.

10. The method of claim 1, where the session is repeated daily/every other day/semi-weekly/weekly.

11. The method of claim 1, further comprising:
    determining if the temperature of at least a portion of the one or more orthodontic aligner is above a predetermined threshold value while the mouthpiece is positioned over the one or more orthodontic aligner; and
    adjusting the parameters of the light based upon the determination.

12. The method of claim 1, further comprising:
    determining the configuration of the one or more orthodontic aligner according to orthodontic treatment plan data; and
    adjusting light radiation of each light emitting element individually based upon the determination.

13. The method of claim 1, wherein the instructions further comprise gently biting down on the mouthpiece to help seat the one or more orthodontic aligner.

14. The method of claim 1, wherein the one or more orthodontic aligner includes a retainer.

15. The method of claim 1, wherein the one or more orthodontic aligner includes an aligner being seated for the first time on the patient's dentition.

16. The method of claim 1, wherein the one or more orthodontic aligner includes an aligner being seated on the patient's dentition after a period of not wearing an aligner.

* * * * *